United States Patent [19]

Warriner

[11] Patent Number: Plant 5,842

[45] Date of Patent: Dec. 30, 1986

[54] ROSE PLANT JACADE

[75] Inventor: William A. Warriner, Tustin, Calif.

[73] Assignee: Jackson & Perkins Company, Medford, Oreg.

[21] Appl. No.: 602,922

[22] Filed: Apr. 23, 1984

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Manford R. Haxton

[57] ABSTRACT

A hybrid tea rose variety having an upright plant, clear pink flower color, heavy petal substance, little fragrance and moderately prickly stems.

1 Drawing Figure

This present invention relates to a new and distinct variety of rose plant of the hybrid tea class which was originated by crossing an unnamed variety with an unnamed variety.

The primary object of this breeding was to produce a new rose variety of exhibition form, with flowers of a clear pink color, plant of upright habit and good vigor. This objective was substantially achieved along with other desirable improvements as characteristics which are outstanding in the new variety and which distinguish it from its parents as well as from all other varieties of which I am aware:

1. Its plant of upright growth.
2. Spiral opening buds.
3. Clear pink color from bud to finished flower.
4. Little fragrance.
5. Good resistance to rose powdery mildew.
6. Large amount of downward hooked prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in October.

Blooming habit: Continuous.

Bud:

*Size.*—1¼" when petals start to unfurl.

*Form.*—Long.

*Color.*—When sepals first divide near Red Purple 64D with large white area near petal base. When half blown; upper side of petals near Red Purple 62C; base of petals near white; lower side of petals Red Purple 63C.

*Sepals.*—Color: Green 138A. Three appendaged sepals lightly appendaged. Two appendaged sepals hairy edged.

*Receptacle.*—Color: Green 138A. Shape: Funnel. size: Long, slender. Surface: Nearly smooth with few stipitate glands.

*Peduncle.*—Length: Medium to short. Surface: Prickly. Color: Light green, bronzy. Strength: Stiff, erect.

*Opening.*—Exhibition type, spiral rollback of petals.

Open bloom:

*Size.*—Medium. Average open size 4".

*Borne.*—Singly.

*Stems.*—Medium, strong.

*Form.*—When first open, high center. Permanence: Flattens, outer petal edges slightly curled.

*Petalage.*—Number of petals under normal conditions: approximately 25–30.

*Color.*—Center of flower, upper side of petals, Pink — near RHS Red Purple 62C; reverse side of petals remains near Red Purple 64C to 64D. Base of petals near white with some yellow pigment at point of attachment. Major color tonality in dictionary terminology is clear pink close to RHS Red Purple 62D.

*Variegations.*—None.

*Discoloration.*—General tonality at end of first day: Very little change. Third day: Color becomes only slightly lighter in intensity than Red Purple Group 62D.

*Fragrance.*—Slight.

Petals:

*Texture.*—Thick

*Shape.*—Round.

*Form.*—Edges slightly quilled.

*Arrangement.*—Imbricated. Petaloids in center, many.

*Persistence.*—Drop off cleanly.

*Lastingness.*—On the plant, long. As cut flower, long.

Reproductive parts:

*Anthers.*—Medium. Color: Yellow. Arrangement: Regular around styles.

*Filaments.*—Color: White.

*Pollen.*—Lemon yellow.

*Styles.*—Color: Near white.

*Stigmas.*—Color: White.

PLANT

Form: Bush.

Growth: Vigorous, upright.

Foliage: Number of leaflets on normal mid-stem leaves: 5–7.

*Size.*—Medium.

*Quantity.*—Normal.

*Color.*—New foliage: Greyed Purple 187B. Old foliage: Green 137A.

Leaflets:

*Shape.*—Pointed elliptic.

*Texture.*—Leathery.

*Edge.*—Serrated.

*Serration.*—Single, small.

*Petiole.*—Rachis: Color: Green. Underside: Prickles.

*Stipules.*—Long, bearded.

*Disease resistance.*—Resistant to mildew, blackspot, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Long, hooked downward.

*Color when young.*—Brown.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its upright plant bearing clear pink blooms of heavy petal subtance, spiral opening form, little fragrance, and moderately prickly stems.

* * * * *

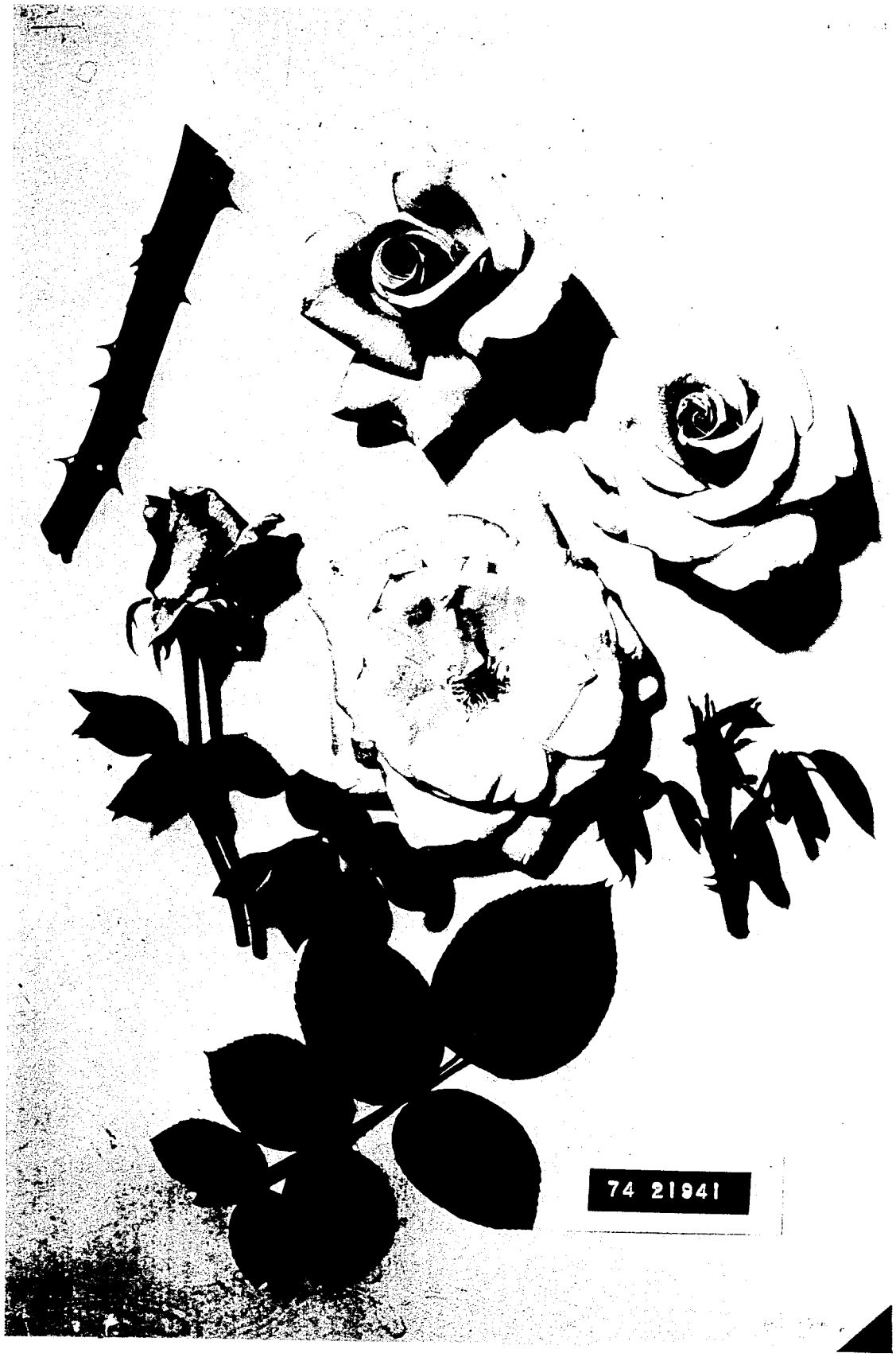
74 21941

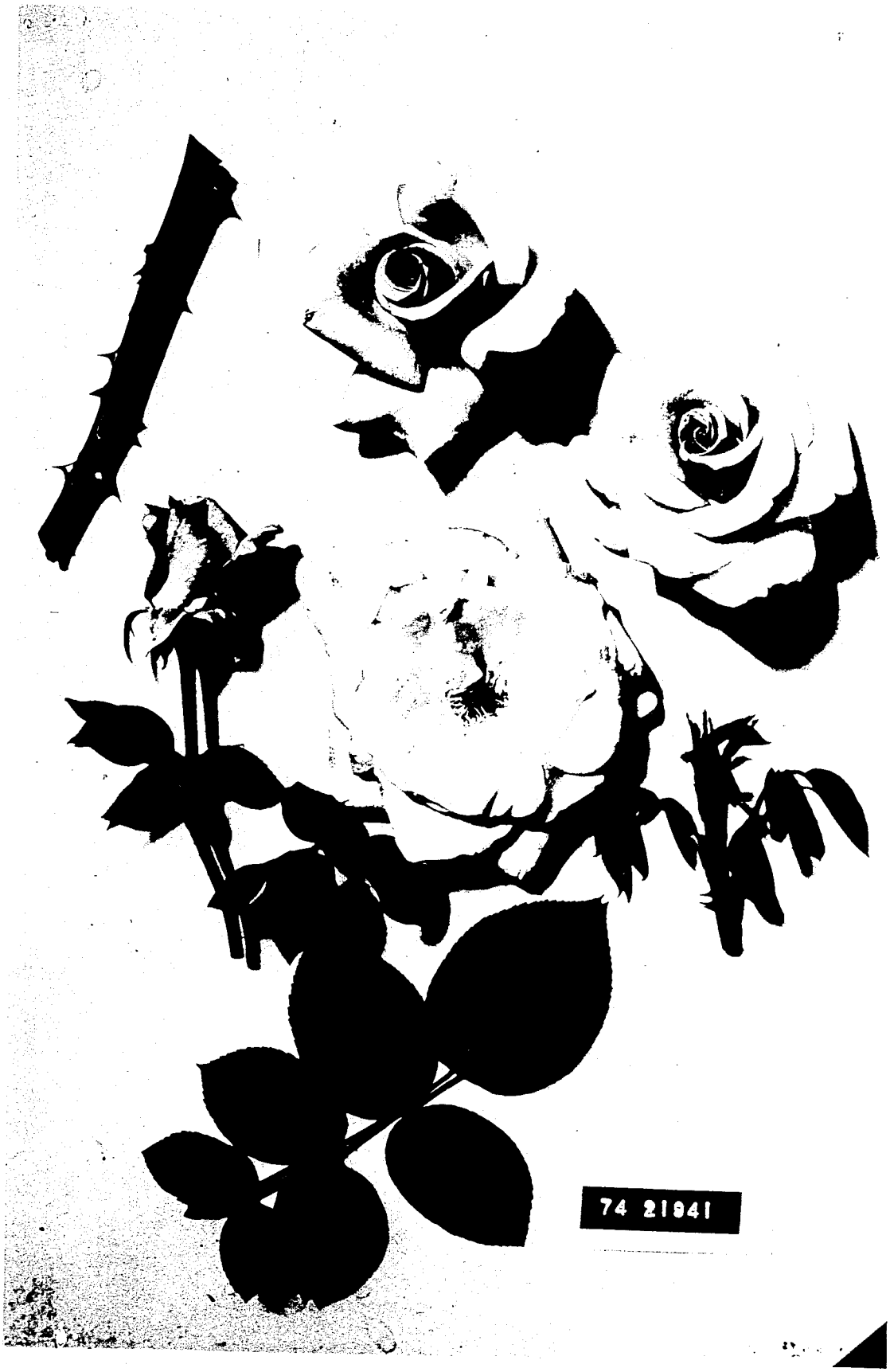
74 21941